United States Patent [19]

Birum

[11] 4,032,601
[45] June 28, 1977

[54] PROCESS FOR THE PRODUCTION OF SULFONAMIDE PHOSPHONATES

[75] Inventor: Gail H. Birum, Kirkwood, Mo.

[73] Assignee: Monsanto Company, St. Louis, Mo.

[22] Filed: Aug. 18, 1975

[21] Appl. No.: 605,694

Related U.S. Application Data

[63] Continuation-in-part of Ser. No. 386,255, Aug. 6, 1973, abandoned.

[52] U.S. Cl. .................. 260/969; 260/397.7 R; 260/556 A; 260/556 AR; 260/944
[51] Int. Cl.² .......................................... C07F 9/40
[58] Field of Search .............. 260/397.7 R, 556 A, 260/556 AR, 944, 969

[56] References Cited

UNITED STATES PATENTS

| | | | |
|---|---|---|---|
| 3,268,450 | 8/1966 | Sims et al. | 260/944 X |
| 3,763,108 | 10/1973 | Chang et al. | 260/969 X |
| 3,870,771 | 3/1975 | Golborn et al. | 260/969 X |

Primary Examiner—Richard L. Raymond
Attorney, Agent, or Firm—Herman O. Bauermeister

[57] ABSTRACT

The present invention concerns a new process for the production of organophosphorus compounds having sulfonamide substituents.

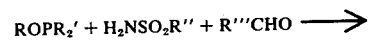

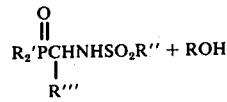

where
R is aryl or chloroalkyl of 2 to 10 carbon atoms,
R' is aryl, aryloxy or chloroalkyloxy of 2 to 10 carbon atoms,
R" is alkyl, aryl, haloaryl or alkaryl of 1 to 15 carbon atoms, where the aryl halogen is bromine, chlorine or fluorine, and R''' is hydrogen alkyl, alkenyl or aryl of 1 to 15 carbon atoms and substituted aryl forms wherein the substituent is fluorine, bromine, chlorine, hydroxyl, alkyloxy or mixtures of such substituents.

These sulfonamide phosphorus compounds have utility as fire-retardants and as biologically active materials.

3 Claims, No Drawings

PROCESS FOR THE PRODUCTION OF SULFONAMIDE PHOSPHONATES

The present application is a continuation-in-part of Ser. No. 386,255, filed Aug. 6, 1973, now abandoned. The present invention relates to a new process for the production of organophosphorus compounds having sulfonamide substituents.

The general method for the production of the novel sulfonamide-containing organophosphorus compositions is in accordance with the following equation:

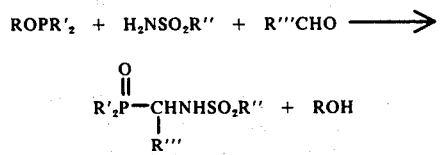

where
R is aryl or chloroalkyl of 2 to 10 carbon atoms,
R' is aryl, aryloxy or chloroalkyloxy of 2 to 10 carbon atoms,
R'' is alkyl, aryl, haloaryl or alkaryl of 1 to 15 carbon atoms, where the aryl halogen is bromine, chlorine or fluorine, and
R''' is hydrogen alkyl, alkenyl or aryl of 1 to 15 carbon atoms and substituted aryl forms wherein the substituent is fluorine, bromine, chlorine, hydroxyl, alkyloxy or mixtures of such substituents.

A specific compound is diphenyl α-(methylsulfonylamino) benzylphosphonate which is prepared from triphenyl phosphite, methanesulfonamide, and benzaldehyde according to the following equation:

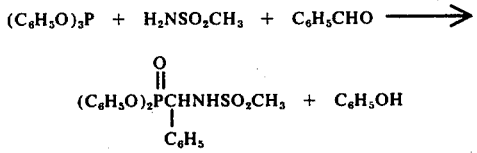

When a phosphonite ester is used as the trivalent phosphorus ester reactant, the product is a phosphinate as illustrated by the formation of phenyl [1-(p-tolylsulfonylamino)ethyl] phenylphosphinate from diphenyl phenylphosphonite, p-toluenesulfonamide, and acetaldehyde:

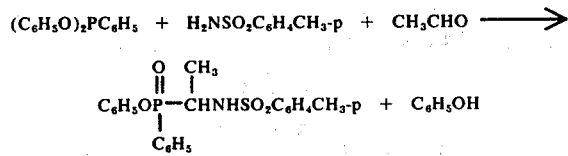

Phosphine oxides are produced when phosphinite esters are used. For example, diphenyl-1-(p-tolylsulfonylamino)butylphosphine oxide is obtained from phenyl diphenylphosphinite, p-toluenesulfonamide, and n-butraldehyde:

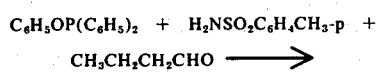

CH₃CH₂CH₂CHO ⟶

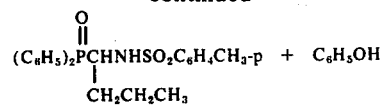

Formation of the products of this invention is usually initiated when a mixture of the three reactants, preferably in an inert solvent such as toluene and chlorobenzene, is warmed to about 70° C. Reaction is usually complete after an hour at 80°–120° C., but warming at higher or lower temperatures is sometimes advantageous. For the less reactive trivalent phosphorus esters, such as the chloroalkyl esters, the use of acid catalysts may be beneficial, particularly boron trifluoride etherate or carboxylic acids such as acetic acid, propionic acid, butyric acid, and benzoic acid.

Gradual addition of the aldehyde reactant to a stirred mixture of the phosphorus ester and sulfonamide reactants in a solvent at reaction temperature, usually from about 70° to 120° C., sometimes aids in control of heat of reaction.

Specific examples showing the preparation and isolation of representative compounds of the present invention are set forth herewith, but are not limitative of the scope of the invention.

EXAMPLE 1

Diphenyl 1-(p-tolylsulfonylamino)butylphosphonate

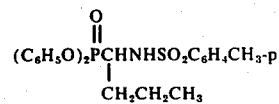

A mixture of 0.5 mole each of triphenyl phosphite, n-butyraldehyde and p-toluenesulfonamide in 150g of chlorobenzene is stirred and warmed under nitrogen. An exothermic reaction is detectable at 85° C., and cooling is used for a few minutes to keep the temperature below 93°. Heating is then continued at 95°–100° for 0.75 hr to ensure complete reaction. The reaction mixture is cooled to 25° and filtered. The product is recrystallized from acetonitrile, giving 202g (88% yield) of white solid: mp 178°–180°; ³¹P nmr(DMSO-d₆) −17.7 ppm.

Anal. Calcd for $C_{23}H_{26}NO_5PS$: C, 60.12; H, 5.70; N, 3.05; P, 6.74; S, 6.98. Found: C, 59.87; H, 5.67; N, 2.90; P, 6.64; S, 6.95.

EXAMPLE 2

Diphenyl 1-(phenylsulfonylamino)butylphosphonate

This product is obtained in 64% yield under conditions similar to those used in the preceding example except that benzenesulfonamide is used in the present example. It is a white solid: mp 173°–175°; ³¹P nmr −17.5 ppm.

EXAMPLE 3

Diphenyl 1-(p-acetamidophenylsulfonylamino)butylphosphonate

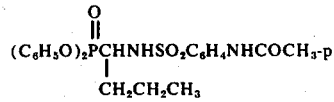

When a mixture of 0.25 mole each of triphenyl phosphite, n-butraldehyde and p-acetamidobenzenesulfonamide in 150g of benzonitrile is warmed under nitrogen, heat of reaction is observed at 115°–120° C., and the solid starting material dissolves. An additional 3g of butraldehyde is added, and the reaction mixture is warmed at 125°–130° for 1.5 hrs. The solvent and most of the by-product phenol are then removed by distillation to 100° at 0.2mm, and the remainder is recrystallized from acetonitrile, giving 65g (52% yield) of crude product. A second recrystallization from acetonitrile gives a white solid: mp 183°–186°; $^{31}$P nmr(DMSO-d$_6$) −17.5 ppm.

Anal. Calcd for $C_{24}H_{27}N_2O_6PS$: C, 57.36; H, 5.42; N, 5.57; P, 6.16; S, 6.38. Found: C, 57.76; H, 5.73; N, 5.57; P, 6.22; S, 6.47.

EXAMPLE 4

Diphenyl 1-p-chlorophenylsulfonylamino)propylphosphonate

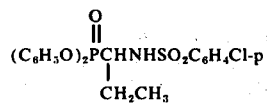

When a mixture of 0.25 mole each of triphenyl phosphite and p-chlorobenzenesulfonamide and 0.275 mole of redistilled propionaldehyde in 150g of chlorobenzene is warmed, heat of reaction is observed at 85°–90°. The temperature is kept at 95°–100° for 1 hr, and then the solvent is removed at reduced pressure. Acetonitrile (150ml) is added to the residue, and the solution is cooled and filtered, giving 50g of solid product. Recrystallization of a portion from acetonitrile gives a white solid: mp 136°–138°; $^{31}$P nmr(DMSO-d$_6$) −17.3 ppm.

Anal. Calcd for $C_{21}H_{21}ClNO_5PS$: C, 54.14; H, 4.54; Cl, 7.61; N, 3.01; P, 6.65; S, 6.88. Found: C, 54.37; H, 4.63; Cl, 7.68; N, 2.82; P, 6.73; S, 6.99.

EXAMPLE 5

Diphenyl 1-(p-fluorophenylsulfonylamino)propylphosphonate

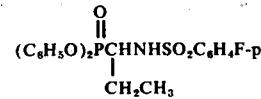

This product is prepared under conditions similar to those used in the preceding example except that p-fluorobenzenesulfonamide is used in the present case. It is a white solid: mp 147.5°–151°; $^{31}$P nmr(DMSO-d$_6$) −17.3 ppm.

EXAMPLE 6

Diphenyl p-tolylsulfonylaminomethylphosphonate

When a mixture of 77.6g of triphenyl phosphite, 8.2g of paraformaldehyde, and 42.8g of p-toluenesulfonamide in 150g of chlorobenzene is warmed, heat of reaction is observed at about 95° C., and cooling is needed for a few minutes to keep the temperature below 105°. Warming is continued at 95°–105° for 1 hr and then the solvent and most of the by-product phenol is removed at reduced pressure.

Recrystallization of the residue from acetonitrile gives 45.8g (44% yield) of white solid: mp 143°–146°; $^{31}$P nmr(DMSO-d$_6$ −15.4 ppm (t, J$_{P-H}$ = 11 Hz); $^1$H nmr δ8.4(t, 1, J = 6Hz, NH), 7.2–7.5(m, 14, aryl), 3.7(d of d, 2, J = 6 and 11 Hz, CH$_2$), and 2.3(s, 3, CH$_3$).

EXAMPLE 7

Bis(2-chloroethyl) 1-(p-tolylsulfonylamino)butylphosphonate

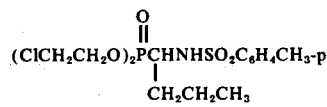

When a mixture of 0.15 mole each of tris(2-chloroethyl) phosphite, n-butyraldehyde and p-toluenesulfonamide in 100g of chlorobenzene is warmed at 100° C. for 1 hr, most of the p-toluenesulfonamide is recovered and $^{31}$P nmr measurement shows that only a small amount of the phosphite has reacted as desired.

When the reaction is repeated under about the same conditions except that 3.0g of acetic acid is added to the reaction mixture before heating is started, the desired reaction occurs as indicated by a major $^{31}$P nmr signal at −24.5 ppm. The solvent and by-product are removed at reduced pressure, and ether is added, causing a solid to separate. This solid is washed with water and then recrystallized from isopropyl alcohol, giving a white solid: mp 85°–88°; $^{31}$P nmr (DMSO-d$_6$) −14.3 ppm.

EXAMPLE 8

Bis(2-chloroethyl) 1-(p-chlorophenylsulfonylamino)ethylphosphonate

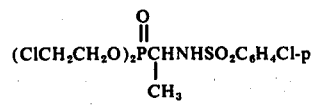

When a mixture of 32.3g of tris(2-chloroethyl phosphite, 5.8g of freshly distilled acetaldehyde, 22.9g of p-chlorobenzenesulfonamide, and 3.0g of acetic acid in 100g of chlorobenzene is stirred and warmed, heat of reaction is observed at about 90°. The temperature is kept at 95°–103° for 1 hr, and then the solvent and by-product are removed at reduced pressure. Ether is added to the residue, causing a solid to separate. This is washed with water and recrystallized from isopropyl alcohol, giving 12.4g of white solid product: mp 94.5°–98°; $^{31}$P nmr (DMSO-d$_6$) −24.0 ppm.

EXAMPLE 9

Bis(2-chloroethyl) 1-(methylsulfonylamino)butylphosphonate

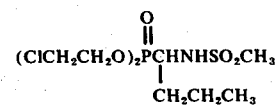

A mixture of 74.1g (0.275 mole) of tris(2-chloroethyl phosphite, 19.8g (0.275 mole) of n-butyraldehyde, and 23.8g (0.25 mole) of methanesulfonamide in 130 ml of chlorobenzene is stirred and warmed at

EXAMPLE 10

Diphenyl 1-(methanesulfonylamino)propylphosphonate

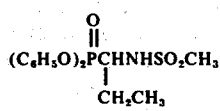

When a mixture of 0.3 mole each of triphenyl phosphite, propionaldehyde, and methanesulfonamide in 150g of chlorobenzene is stirred and warmed under nitrogen, heat of reaction is observed at about 100° C., and cooling is used for a few minutes to keep the temperature below 110° C., and cooling is used for a few minutes to keep the temperature below 110°. Warming is continued at 100°–110° for 2 hrs, and then the reaction mixture is stirred as it cools to room temperature, resulting in formation of a solid, 53.4g (48% yield), of crude product. This is washed with water and recrystallized from benzene, giving white solid product: mp 136°–139°; $^{31}$P nmr (DMSO-$d_6$) −17.3 ppm.

Anal. Calcd for $C_{16}H_{20}NO_5PS$: C, 52.03; H, 5.46; N, 3.79; P, 8.38; S, 8.68. Found: C, 52.53; H, 5.34; N, 3.63; P, 8.11; S, 8.30.

EXAMPLE 11

Diphenyl (α-methylsulfonylamino)benzylphosphonate

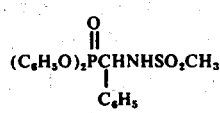

When equimolar quantities of triphenyl phosphite, benzaldehyde, and methanesulfonamide in chlorobenzene are warmed at 110°–117° for 0.5 hr, a 51% yield of crude product is isolated from the reaction mixture. The product is washed with water and recrystallized from chlorobenzene, giving a 38% yield of white solid: mp 179°–181°; $^{31}$P nmr(DMSO-$d_6$) −13.7 ppm (d, J = 26Hz); $^1$H nmr δ8.9(d of d, 1, J = 2 and 11Hz, NH), 6.8–7.7(m, 15, aryl), 5.3(d of d, 1, J = 10 and 24Hz, CH), 2.7 (s, 3, CH$_3$).

EXAMPLE 12

Bis(p-tolyl) 1-(-tolylsulfonylamino)ethylphosphonate

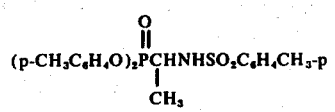

A mixture of 0.1 mole each of tris(p-tolyl) phosphite, acetaldehyde, and p-toluenesulfonamide in 100g of chlorobenzene is stirred under nitrogen while being warmed at 95°–100° C. for 1.5 hrs. The solvent is stripped at reduced pressure, and the residue is diluted with ether, causing separation of 25.9g (56% yield ) of cured product. Recrystallization of a portion from isopropyl alcohol gives a white solid: mp 114°–116.5°; $^{31}$P nmr (DMSO-$d_6$) −17.7 ppm.

When an equimolar mixture of tris(p-tolyl) phosphite, vanillin, and n-butylsulfonamide are similarly treated, the product is bis(p-tolyl) α-butylsulfonylamino-4-hydroxy-3-methoxybenzylphosphonate. Similar treatment of an equimolar mixture of tris(2-chloropropyl) phosphite, 3,4-dichlorobenzaldehyde, and p-bromobenzenefulfonamide in toluene gives bis(2-chloropropyl) α-(p-bromophenylsulfonylamino)-3,4-dichlorobenzylphosphonate.

EXAMPLE 13

Phenyl [1-(p-tolylsulfonylamino)ethyl]phenylphosphinate

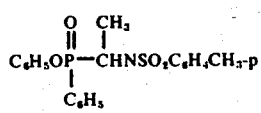

A mixture of 0.15 mole each of diphenyl phenylphosphonite, acetaldehyde, and p-toluenesulfonamide in 100g of chlorobenzene is stirred and warmed at 103°–115° C. for 1 hr, and the solvent and by-product phenol are removed by concentration of the reaction mixture to 120° at 0.5mm. Ether is stirred into the residue, causing separation of 49.4g (79% yield) of solid product. Recrystallization twice from chlorobenzene gives a white solid: mp 178°–181°; $^{31}$P nmr (DMSO-$d_6$) −37.7 ppm.

EXAMPLE 14

Diphenyl-1-(p-tolylsulfonylamino)butylphosphine oxide

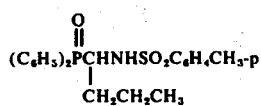

A white solid (60.6g, 71% yield) separates when a mixture of 0.2 mole each of phenyl diphenylphosphinite, n-butyraldehyde, and p-toluenesulfonamide in 125g of chlorobenzene is warmed at 105° C. for 1 hr. Recrystallization three times from o-dichlorobenzene gives a white solid product: mp 254°–263°; $^{31}$P nmr (CF$_3$CO$_2$H) −44.7 ppm.

Anal. Calcd for $C_{23}H_{26}NO_3PS$: C, 64.62; H, 6.13; N, 3.28; P, 7.24; S, 7.50. Found: C, 64.41; H, 6.16; N, 3.20; P, 7.22; S, 7.49.

EXAMPLE 15

Diphenyl 1-(p-tolylsulfonylamino)-2-methyl-2-propenylphosphonate

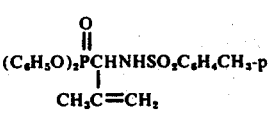

Crude solid product (481.g, 35% yield) is isolated after a mixture of 0.3 mole each of triphenyl phosphite, methacrolein, and p-toluenesulfonamide in 175g of chlorobenzene is warmed at 95°–100°, stripped at reduced pressure, and diluted with ether. Recrystallization once from isopropyl alcohol and twice from chlorobenzene gives a white solid: mp 125°–133°; $^{31}$P nmr(DMSO-d$_6$) −21.4 ppm.

Anal. Calcd. for C$_{23}$H$_{24}$NO$_5$PS: C, 60.38; H, 5.29; N, 3.06; P, 6.77; S, 7.01. Found C, 60.16; H, 5.26; N, 2.93; P, 6.82; S, 6.93.

When dodecyl aldehyde is used in place of methacrolein, the product is diphenyl 1-(p-tolylsulfonylamino)-dodecylphosphonate.

The nitrogen-containing organophosphorus compounds of the present invention are useful as fire-retardants and as biological toxidants. The following examples illustrate the use of typical products.

EXAMPLE 16

Pre-emergent herbicidal activity of representative compounds of this invention is determined by the following procedure:

A good grade of top soil is placed in aluminum pans and compacted to a depth of ⅜ to ½ inch from the top of the pan. A pre-determined number of seeds of each of several plant species are placed on top of the soil in the pans. The seeds are covered with soil and the pans leveled. The herbicidal composition is applied by spraying the surface of the top layer of soil with a solution containing a sufficient amount of active ingredient to obtain a rate of application of 10 lbs. per acre. The pans are then placed on a sand bench in the greenhouse and watered from below as needed. The plants are observed at the end of approximately 14 days and the results recorded.

Pre-emergent activity of the compounds prepared in the designated Examples is observed against the species as shown in the table below, wherein X denotes that herbicidal activity is observed.

| COMPOUND OF EXAMPLE | PRE-EMERGENT TESTING | | | |
|---|---|---|---|---|
|  | 13 | 4 | 9 | 1 |
| Canada Thistle |  |  |  | X |
| Lambsquarters |  | X | X |  |
| Johnsongrass |  |  | X |  |
| Downy Brome |  |  | X | X |
| Barnyardgrass |  |  | X |  |

EXAMPLE 17

A preliminary fire-retardant test is conducted as follows:

A 2 × 8 inch strip of cotton cloth is padded with a solution of equal parts of the test compound and 37% formalin, and the strip is dried at 65° C and then cured at 140° C for 0.5 hr. This is followed by washing with water and then drying to constant weight. This treated sample is applied to a Bunsen burner and then removed from the combustion zone of the burner after 5 seconds exposure to the flame. A sample which is self-extinguishing after this treatment is considered to pass the test. When Bis(2-chloroethyl) 1-(p-chlorophenylsulfonylamino)ethylphosphonate is used, and the add-on is about 18%, the sample passes the test. Other representative compounds of the invention which have fire-retardant properties are bis(2-chloroethyl) 1-(methylsufonylamino)butylphosphonate and bis(2-chloropropyl) α-(p-bromophenylsulfonylamino)-3,4-dichlorobenzylphosphonate.

Compounds of this invention that contain at least ten percent halogen (especially chlorine and bromine) are particularly useful as fire-retardants.

Those that contain less than ten percent halogen are also useful as synergists in enhancing the fire-retardance of halogen-containing polymers. For example, the fire retardant property of polyvinyl chloride is improved by use of materials of this invention, which provide the advantage of introducing phosphorus, for example in the proportion of about 1 % to 10 % by weight relative to the polyvinyl chloride. Compounds useful for this purpose include diphenyl 1-(p-chlorophenylsulfonylamino)propylphosphonate, diphenyl p-tolylsulfonylaminomethylphosphonate, bis(2-chloroethyl) 1-(methylsulfonylamino)butylphosphonate, phenyl [1-(p-tolylsulfonylamino)ethyl]phenylphosphinate, diphenyl 1-(p-acetamidophenylsulfonylamino)butylphosphonate, diphenyl 1-(p-fluorophenylsulfonylamino)propylphosphonate, bis(2-chloroethyl) 1-(p-tolylsulfonylamino)butylphosphonate, diphenyl 1-(methanesulfonylamino)propylphosphonate, bis(p-tolyl) α-butylsulfonylamino-4-hydroxy-3-methoxy-benzylphosphonate, and diphenyl 1-(p-tolylsulfonylamino)dodecylphosphonate.

What is claimed is:

1. Process for the production of:

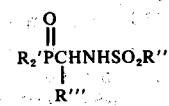

where
R' is aryl, aryloxy or chloroalkyloxy of 2 to 10 carbon atoms,
R" is alkyl, aryl, haloaryl, or alkaryl of 1 to 15 carbon atoms, where the aryl halogen is bromine, chlorine or fluorine, and
R"' is hydrogen, alkyl, alkenyl or aryl of 1 to 15 carbon atoms and substituted aryl forms wherein the substituent is fluorine, bromine, chlorine, hydroxyl, alkyloxy or mixtures of such substituents, which comprises heating a mixture containing R$_2$'λPOR, R"'CHO and H$_2$NSO$_2$R" where R is aryl or chloroalkyl of 2 to 10 carbon atoms, in the presence of an acid catalyst selected from the group consisting of boron trifluoride etherate, acetic acid, propionic acid, butyric acid and benzoic acid.

2. Process for the production of:

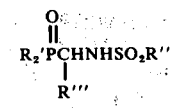

where
R' is aryl, aryloxy or chloroalkyloxy of 2 to 10 carbon atoms,
R" is alkyl, aryl, haloaryl or alkaryl of 1 to 15 carbon atoms, where the aryl halogen is bromine, chlorine or fluorine, and
R"' is hydrogen, alkyl, alkenyl or aryl of 1 to 15 carbon atoms and substituted aryl forms wherein the sutstituent is fluorine, bromine, chlorine, hydroxyl, alkyloxy or mixtures of such substituents, which comprises heating a mixture containing R$_2$'λPOR,
R"'CHO and H$_2$NSO$_2$R" where R is aryl or chloroalkyl of 2 to 10 carbon atoms in the presence of an acid catalyst selected from the group consisting of acetic acid, propionic acid, and butyric acid.

3. Process for the production of:

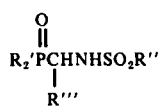

where

R' is aryl, aryloxy or chloroalkyloxy of 2 to 10 carbon atoms,

R'' is alkyl, aryl, haloaryl or alkaryl of 1 to 15 carbon atoms, where the aryl halogen is bromine, chlorine or fluroine, and R''' is hydrogen, alkyl, alkenyl or aryl of 1 to 15 carbon atoms and substituted aryl forms wherein the substituent is fluorine, bromine, chlorine, hydroxyl, alkyloxy or mixtures of such substituents, which comprises heating a mixture containing $R_2'\lambda POR$, $R'''CHO$ and $H_2NSO_2R''$ where R is aryl or chloroalkyl of 2 to 10 carbon atoms in the presence of acetic acid as a catalyst.

* * * * *